United States Patent [19]

Inoue et al.

[11] Patent Number: 4,778,269
[45] Date of Patent: Oct. 18, 1988

[54] METHOD FOR DETERMINING CRYSTAL ORIENTATION

[75] Inventors: Yasuo Inoue; Tadashi Nishimura; Kazuyuki Sugahara; Shigeru Kusunoki, all of Hyogo, Japan

[73] Assignee: Mitsubishi Denki Kabushiki Kaisha, Tokyo, Japan

[21] Appl. No.: 11,511

[22] Filed: Feb. 6, 1987

[30] Foreign Application Priority Data

Feb. 8, 1986 [JP] Japan ................................ 61-26166
Apr. 14, 1986 [JP] Japan ................................ 61-85785

[51] Int. Cl.$^4$ .......................... G01J 3/44; G01N 21/65
[52] U.S. Cl. ........................................ 356/31; 356/301
[58] Field of Search .................................. 356/31, 301

[56] References Cited

PUBLICATIONS

*Appl. Phys. Lett.*, vol. 44, 1984, pp. 535–537 by J. B. Hopkins et al.
*Appl. Phys. Lett.*, vol. 59, 1986, pp. 1103–1110 by J. B. Hopkins et al.

*Primary Examiner*—F. L. Evans
*Attorney, Agent, or Firm*—Lowe, Price, LeBlanc, Becker & Shur

[57] ABSTRACT

In a method for determining orientation of a crystal with polarization selective Raman microprobe spectroscopy, polarization angles of both light incident on the crystal and Raman scattered light emitted from the crystal are varied coincidently in ordinary circumstances and only either one of the polarization angles is varied in only case that intensity of the scattered beam does not change substantially in spite of the coincident variation of both the polarization angles.

3 Claims, 5 Drawing Sheets

METHOD FOR DETERMINING CRYSTAL ORIENTATION

BACKGROUND OF THE INVENTION

1. Field of the Invention

The present invention relates to a method for determining crystal orientation, and more particularly to improvement in a method which utilize polarization selective Raman microprobe spectroscopy.

2. Description of the Prior Art

Raman microprobe determination of crystal orientation is described, e.g., in *Appl. Phys. Lett.*, vol. 44, 1984, pp. 535–537 by J. B. Hopkins et al. and *J. Appl. Phys.*, vol. 59, 1986, pp. 1103–1110 by J. B. Hopkins et al.

The Raman scattering intensity I is expressed by the following formula:

$$I \alpha \sum_j (e_1 R^j e_2)^2 \qquad (1)$$

where $e_1$ and $e_2$ are the polarization vectors of the incident light and the scattered light respectively, and $R^j$ represents a Raman tensor.

Referring to FIG. 1, there is shown a conceptional perspective view illustrating the geometrical relation between the polarizations of incident light and scattered light. Incident light 1 is focused on a specimen 5 of silicon or the like, and Raman scattered light 3 is emitted from the crystal 5. On this occasion, the incident light 1 has a polarization direction 2 which is rotated by a polarization angle $\psi_1$, from a reference $\psi_0$, while the Raman scattered light 3 has a polarization direction 4 which is rotated by a polarization angle $\psi_2$ from the same reference $\psi_0$. The scattered light 3 having this polarization direction 4 is selected by a polarization analyzer and the intensity I of the selected light 3 is measured. A series of the intensity measurements represents the polarization characteristic which reflects the crystal orientation. The geometrical relation between the incident light beam 1 and the crystal axes <100> can be determined by fitting a measured intensity profile of the scattered light 3 taken as a function of the polarization angles to that derived from the formula (1) as to known crystal orientation.

Referring to FIG. 2, there is shown a block diagram of an apparatus for determining crystal orientation. A laser beam 12 emitted from a laser source 11 is passed through a spectroscopic filter 13 and the natural light is eliminated. The polarization direction of the filtered beam 12 is controlled by a polarizer 14 and then the beam 12 is expanded by a beam expander 15. The expanded beam is deflected by a half mirror 16 and focused by a lens 17 on a specimen 5 of which crystal orientation is to be determined. At this time, light having spectroscopic energies different from that of the original laser beam 12 is emitted as Raman scattered light from the specimen 5. The Raman scattered light 19 is collected by the lens 17 and deflected by a mirror 20 toward a polarization analyzer 21 in which light having a predetermined polarization direction is selected. The selected Raman scattered light is passed through a depolarizer 22 and focused by a lens 23 on a slit of a spectrometer 24. Spectra separated in the spectrometer 24 are detected by a photodetector 25, and then obtained data are processed by a computer 26 thereby to determine crystal orientation.

During measurements with this apparatus, the polarization direction of only either one of the incident light and the scattered light is systematically varied by correspondingly rotating only either one of the polarizer 14 and the polarization analyzer 21 with the other being fixed. Thus, it takes a long time to analyze the data, and the crystal orientation can not be determined three-dimensionally by one series of the measurements.

SUMMARY OF THE INVENTION

In view of the prior art, it is a major object of the present invention to provide a method with which it takes a shorter time to analyze the data and the crystal orientation can be determined three-dimensionally by only one series of the measurements.

According to the present invention, a method for determining orientation of a crystal with polarization selective Raman microprobe spectroscopy comprises the steps of: polarizing light incident on the crystal by a polarizer; selecting light having a selected polarization direction in Raman scattered light emitted from the crystal by a polarization analyzer; measuring intensity of the selected light; and synchronously rotating both of the polarizer and the polarization analyzer in ordinary circumstances and rotating only either one of the polarizer and the polarization analyzer in only case that the intensity does not change substantially in spite of the synchronous rotation of both the polarizer and the polarization analyzer.

These objects and other objects, features, aspects and advantages of the present invention will become more apparent from the following detailed description of the present invention when taken in conjunction with the accompanying drawings.

DESCRIPTION OF THE PREFERRED EMBODIMENTS

Orientation determination of a silicon crystal is now described by way of example.

Figure 1:
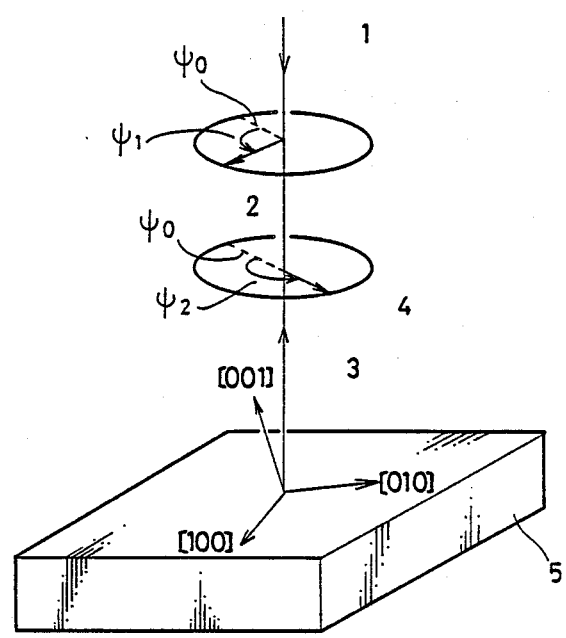
FIG. 1 is a conceptional perspective view illustrating the geometrical relation between the polarizations of incident light and Raman scattered light.
Figure 2:
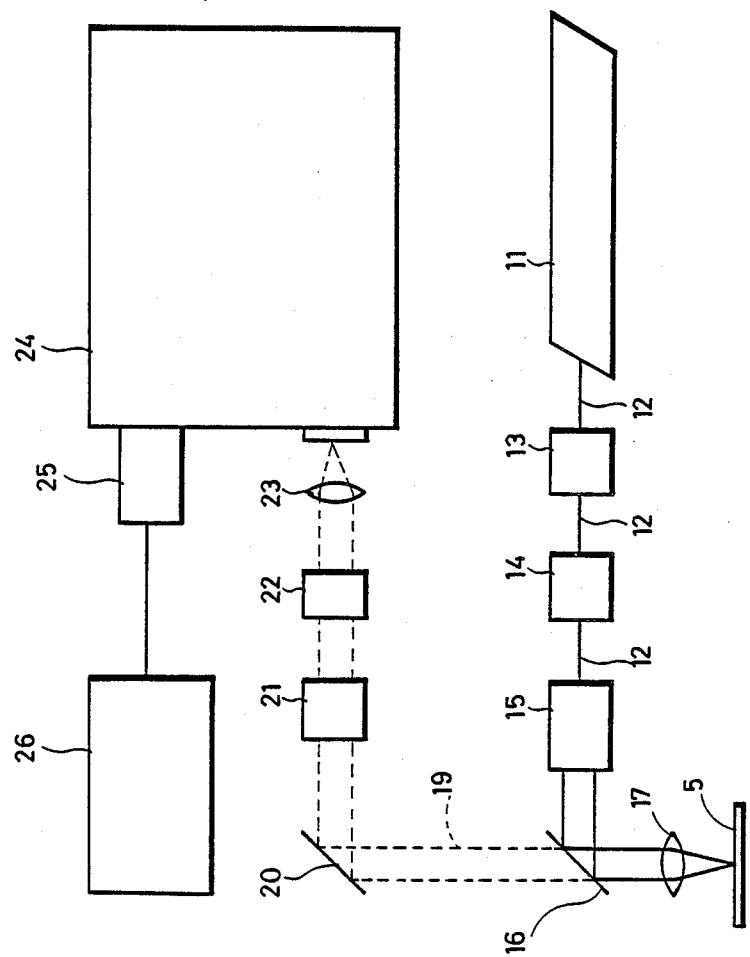
FIG. 2 is a block diagram of an apparatus for determing crystal orientation.
Figure 3:
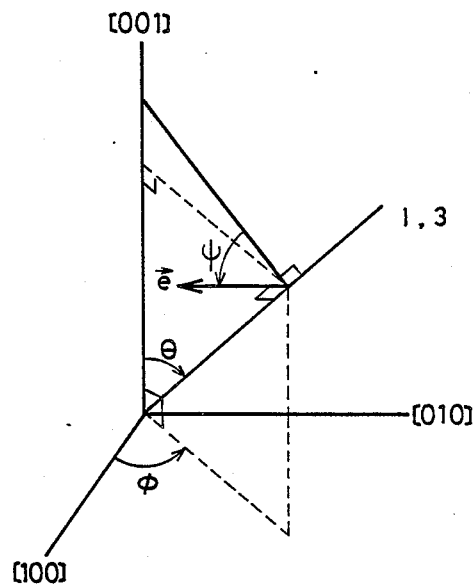
FIG. 3 is a conceptional perspective view illustrating the geometrical relation between a light beam and crystal axes <100>.

Referring to FIG. 3, there is shown the geometrical relation of an incident light beam 1 or a Raman scattered light beam 3 to crystal axes <100>. For convenience of explanation of the theoretical polarization characteristic derived from the formula (1), the polarization angle $\psi$ is defined as shown in this figure. A reference character $\phi$ represents an angle between the [100] axis and a projected line of the beam axis 1 or 3 on the (001) plane, while $\theta$ denotes an angle between the [001] axis and the beam axis 1 or 3. A reference character e indicates the polarization vector which is normal to the beam axis 1 or 3, and the polarization angle $\psi$ is defined as an angle of the polarization vector e to a plane which contains the [001] axis and the beam axis 1 or 3. In other words, when the angles $\theta$, $\phi$ and $\psi$ are known, the crystal orientation is determined three-dmmensionally with respect to the beam axis 1 or 3.

Figure 4:
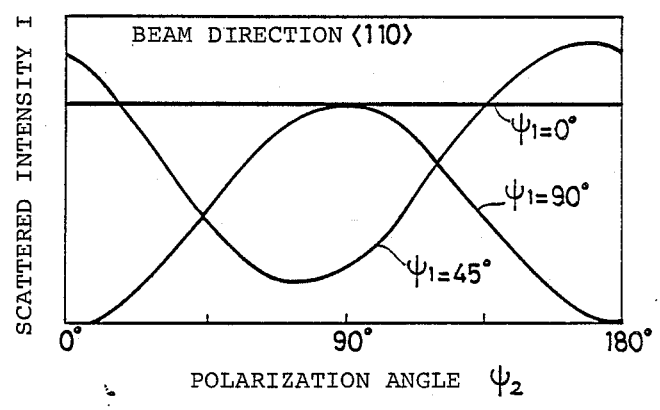
FIG. 4 is a graph showing the polarization characteristic of Raman scattered light on the condition that an incident beam having a fixed polarization angle $\psi_1$ is parallel to an <110> axis and only the selected polarization angle $\psi_2$ of the scattered light is varied.

Referring to FIG. 4, there is shown a graph of polarization characteristic curves with the incident beam being parallel to an <110> axis. In each of these curves, the polarization angle $\psi_1$ of the incident light is fixed to a certain value while the polarization angle $\psi_2$ of the scattered light is varied. In this graph, the horizontal axis indicates the polarization angle $\psi_2$ of the scattered light and the vertical axis indicates the intensity of the scattered light. As seen, different polarization characteristic curves are obtained depending on the different fixed polarization angles $\psi_1$ of the incident beam. Namely, since the polarization angle $\psi_1$ of the incident beam is not known when the orientation of an unknown crystal is going to be determined, it is necessary to fit a measured polarization characteristic curve to a suitable one among various theoretical polarization curves using a computer. Further, when approximately $\psi_1 = 0°$, the scattered intensity I does not change substantially in spite of the variation of the polarization angle $\psi_2$ of the scattered light. Therefore, it is difficult to precisely determine the polarization angles $\psi_1$, $\psi_2$. In other words, it is difficult to precisely determine the crystal orientation in the direction normal to the beam axis.

Figure 5:
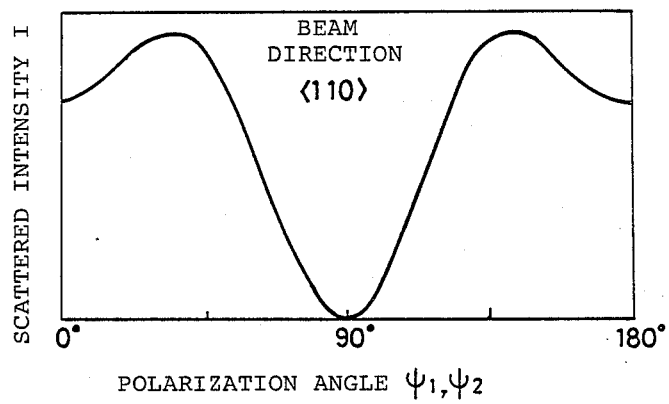
FIG. 5 is a graph similar to that of FIG. 4, but on the condition that both of the polarization angles $\psi_1$, $\psi_2$ of the incident light and scattered light are varied coincidently.

Referring to FIG. 5, there is shown a graph similar to that of FIG. 4, but on the condition that the polarization angles $\psi_1$, $\psi_2$ of the incident light and scattered light both are varied coincidently. On this condition, only one curve is obtained. Namely, since $\psi_1 = \psi_2$, the number of parameters for orientation analysis is decreased by one. Accordingly, the polarization angles $\psi_1$, $\psi_2$ both can be readily determined by fitting a measured curve to that derived from the formula (1). This means that the crystal orientation in the direction normal to the beam axis can be readily determined.

Figure 6:
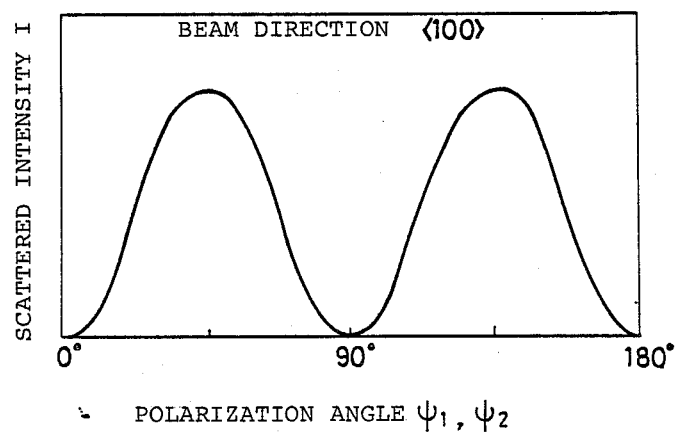
FIG. 6 is a graph similar to that of FIG. 5, but on the condition that the incident beam is parallel to an <100> axis.

Referring to FIG. 6, there is shown a graph similar to that of FIG. 5, but on the condition that the incident beam is parallel to an <100> direction. In this case also, the crystal orientation can be readily determined three-dimentionally by coincidently varying both the polarization angles $\psi_1$, $\psi_2$.

Figure 7:
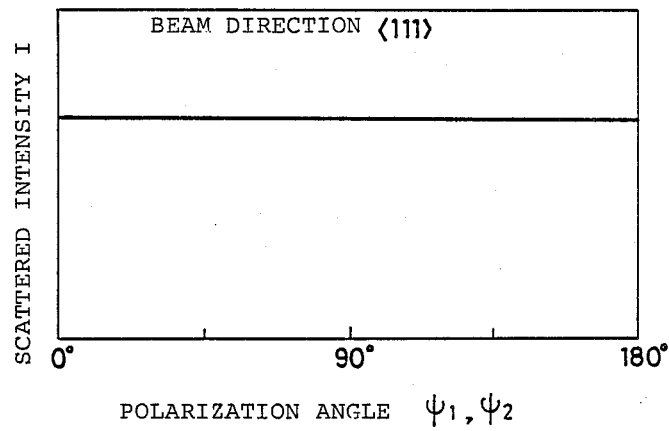
FIG. 7 is a graph similar to that of FIG. 6, but on the condition that the incident beam is parallel to an <111> axis.

Referring to FIG. 7, there is shown a grahh similar to that of FIG. 6, but on the condition that the incident beam is parallel to an <111> direction. On this condition, the scattered intensity I is constant in spite of the coincident variation of both the polarization angles $\psi_1$, $\psi_2$. Therefore, the polarization angles $\psi_1$, $\psi_2$ can not be determined at all by fitting a measured curve to the theoretical curve. In such case, however, the scattered intensity can be varied by varying only either one of the polarization angles $\psi_1$, $\psi_2$ with the other being fixed.

Figure 8:
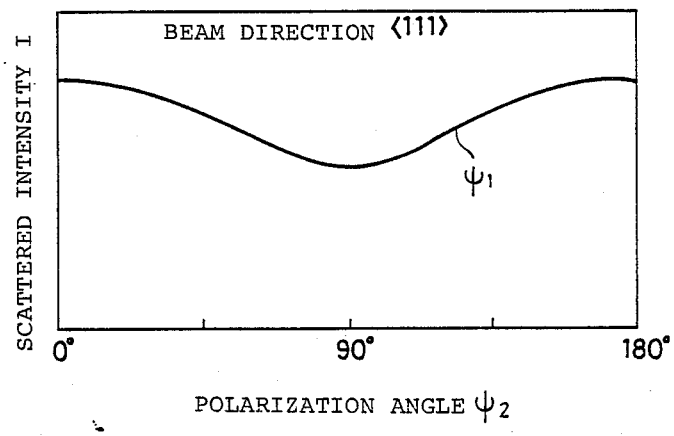
FIG. 8 is a graph similar to that of FIG. 7, but on the condition that the polarization angle $\psi_1$ of the incident beam is fixed to a certain value and only the polarization angle $\psi_2$ of the scattered light is varied.

Referring to FIG. 8, there is shown a graph similar to that of FIG. 7, but on the condition that only the polarization angle $\psi_2$ of the scattered light is varied with the polarization angle $\psi_1$ of the incident beam being fixed to a certain value. As seen in this graph, the scattered intensity varies according as the polarization angle $\psi_2$ is varied. Similarly as described referring to FIG. 4, therefore, the polarization angles $\psi_1$, $\psi_2$ can be determined by fitting a meaured curve to a suitable one among various theoretical curves. Namely, the crystal orientation can be determined even in the direction normal to the light beam and thus determined three-dimentionally.

As described in the above preferred embodiment, both the polarization angles $\psi_1$, $\psi_2$ are varied coincidently in ordinary circumstances and only either one of the angles $\psi_1$, $\psi_2$ is varied in only case that the scattered intensity does not change substantially in spite of the coincident variation of both the angles $\psi_1$, $\psi_2$. However, it will be understood that only one of the polarization angles $\psi_1$, $\psi_2$ may be varied in ordinary circumstances and both of the angles $\psi_1$, $\psi_2$ may be varied in only case that the scattered intensity does not change in spite of the variation of the either one of angles $\psi_1$, $\psi_2$, though the number of parameters for the orientation analysis is increased.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A method for determining orientation of a crystal with polarization selective Raman microprobe spectroscopy, comprising the steps of:
    polarizing light incident on said crystal with a polarizer;
    selecting light having a selected polarization direction in Raman scattered light emitted from said crystal with a polarization analyzer;
    measuring intensity of said selected light; and
    synchronously rotating both of said polarizer and said polarization analyzer and rotating only one of said polarizer and said polarization analyzer in case said intensity does not change substantially in spite of said synchronous rotation of both said polarizer and said polarization analyzer.

2. A method in accordance with claim 1, wherein said light incident on said crystal is a laser beam.

3. A method in accordance with claim 1, wherein said crystal is of silicon or germanium.

* * * * *